US009682032B2

(12) United States Patent
Sawyer et al.

(10) Patent No.: US 9,682,032 B2
(45) Date of Patent: Jun. 20, 2017

(54) CRANIAL DELIVERY OF PHARMACEUTICALS

(71) Applicant: Glia, LLC, Boston, MA (US)

(72) Inventors: Kenneth I. Sawyer, Cushing, ME (US); Wei-wei Chang, Boston, MA (US)

(73) Assignee: Glia, LLC, Boston, MA (US)

( * ) Notice: Subject to any disclaimer, the term of this patent is extended or adjusted under 35 U.S.C. 154(b) by 0 days.

(21) Appl. No.: 14/777,278

(22) PCT Filed: Mar. 14, 2014

(86) PCT No.: PCT/US2014/027280
§ 371 (c)(1),
(2) Date: Sep. 15, 2015

(87) PCT Pub. No.: WO2014/152385
PCT Pub. Date: Sep. 25, 2014

(65) Prior Publication Data
US 2016/0030333 A1  Feb. 4, 2016

Related U.S. Application Data

(60) Provisional application No. 61/790,120, filed on Mar. 15, 2013.

(51) Int. Cl.
A61K 31/56 (2006.01)
A61K 9/00 (2006.01)
A61K 31/352 (2006.01)
A61K 31/57 (2006.01)

(52) U.S. Cl.
CPC .......... *A61K 9/0014* (2013.01); *A61K 31/352* (2013.01); *A61K 31/57* (2013.01)

(58) Field of Classification Search
None
See application file for complete search history.

(56) References Cited

U.S. PATENT DOCUMENTS

| 6,630,507 | B1 | 10/2003 | Hampson et al. |
| 7,632,868 | B2 | 12/2009 | Lipkin et al. |
| 8,222,292 | B2 | 7/2012 | Goskonda et al. |
| 8,236,768 | B2 | 8/2012 | Brown et al. |
| 2005/0203073 | A1 | 9/2005 | Schreiber |
| 2006/0089408 | A1 | 4/2006 | Wei et al. |
| 2006/0093597 | A1 | 5/2006 | Zhu |
| 2008/0132475 | A1 | 6/2008 | Connor et al. |
| 2010/0016264 | A1* | 1/2010 | Connor .................. A61K 45/06 514/170 |

FOREIGN PATENT DOCUMENTS

| EP | 1895960 B1 | 4/2012 |
| WO | WO-2011-055383 A2 | 5/2011 |
| WO | WO-2012-154956 A2 | 11/2012 |
| WO | WO-2014-018856 A1 | 1/2014 |

OTHER PUBLICATIONS

Dr. Foulks, Contact lens intolerance, Feb. 15, 2010.*
Holzer et al "Effects and Side-Effects of 2 Percent Progesterone Cream on the Skin of Peri- and Postmenopausal Women: Results from a Double-Blind, Vehicle-Controlled, Randomized Sutdy" British Journal of Dermatology vol. 153, pp. 626-634. 2005.
Kim et al "Progesterone Produces Antinociceptive and Neuroprotective Effects in Rats with Microinjected Lysophosphatidic Acid in the Trigeminal Nerve Root" Molecular Pain vol. 8, article 16. 2012.
Fischer et al "Effects of a Topically Applied 2% Delta-9-Tetrahydrocannabinol Opthalmic Solution on Intraocular Pressure and Aqueous Humor Flow Rate in Clinically Normal Dogs" American Journal of Veterinary Research vol. 74, pp. 275-280, 2013.

* cited by examiner

*Primary Examiner* — Jean Cornet
(74) *Attorney, Agent, or Firm* — Cesari and McKenna, LLP

(57) ABSTRACT

A method for rapid delivery of an active compound to innervate a cranial nerve of a subject. Also provided is a method for treating a disease or condition by topically applying a pharmaceutical composition to the face excluding the palpebral part of the eye, in an amount effective for treating the disease or condition.

2 Claims, No Drawings

CRANIAL DELIVERY OF PHARMACEUTICALS

CROSS REFERENCE TO RELATED APPLICATIONS

This application is the National Stage of International Application No. PCT/US2014/027280, filed on Mar. 14, 2014, which claims the benefit of U.S. Provisional Application No. 61/790,120, filed on Mar. 15, 2013. The contents of both applications are hereby incorporated by reference in their entirety.

BACKGROUND

The most common routes for administering pharmaceuticals are oral, intramuscular, subcutaneous, intravenous, and transdermal. Each route has its own particular drawback. For example, a drug administered orally is subjected to harsh conditions including exposure to stomach acids and digestive enzymes even before it gets into the bloodstream via the intestinal tract, hepatic portal system, and liver. The digestive system and first pass metabolism can greatly diminish the activity of the pharmaceutical. As a result, larger doses of the drug are required, leading to undesirable side effects. Despite large drug doses, in many instances the drug may still not reach target tissues such as the brain, head, and neck. The area inside the eye and behind the eye are examples of body areas to which it is difficult to deliver a drug effectively.

Typically, ophthalmic drugs in the form of an eye drop or an ointment are applied to the front of the eye, which is designed to protect the eyes from foreign substances. Drugs administered in this manner do not reach inside or behind the eye. More importantly, other typical drug delivery routes do not allow the drug to induce the desired therapeutic effect at the target gland or tissue.

Injectable drugs enter the circulation immediately but can have undesirable systemic effects.

Transdermal methods of delivery allow the absorption of medicine directly through the skin. Gels, emulsions, creams, sprays and patches are easy to use and are effective for transdermal delivery of a drug. However current transdermal delivery routes are utilized for delivering a drug either to exert a local effect or to enter the blood circulation.

Pharmaceuticals administered by all of the routes described above enter the bloodstream. Additionally, drugs in the circulation cannot always reach all areas of the body. For example, many drugs cannot pass through the blood-brain barrier. It also can be difficult to deliver a drug to an area of the body that is not well vascularized.

The need exists for new routes of drug administration that allow for lower doses to be administered and that allow access of the drug to areas of the body which are difficult to treat, such as the brain, eyes, and other head and neck regions.

SUMMARY

One aspect of this invention relates to a method for delivery of a drug which rapidly acts on a cranial nerve of a subject. The method includes the steps of obtaining a topical composition that includes the drug and a pharmaceutically acceptable excipient, and applying the topical composition to an area of the face of the subject not including the palpebral part of the eye.

In one embodiment, a method is provided for treating oropharyngeal dysphagia by administering a cannabinoid to the subject. The cannabinoid is administered topically to the subject on an area of the face not including the palpebral part of the eye.

Also provided is a method for treating a subject having a disease mediated by a neurotropic microbe, e.g., a virus, a bacteria, a fungus, or a mold. In this method, an antimicrobial agent, e.g., an antiviral, an antibacterial, or an antifungal, is topically administered to the subject on an area of the face not including the palpebral part of the eye.

In a further aspect, a method for treating an ophthalmic disease or condition is disclosed. The method is carried out by topically administering an effective amount of a pharmaceutical composition to a subject in need thereof by applying it to an area of the face not including the palpebral part of the eye. The ophthalmic disease or condition that can be treated is glaucoma, allergic conjunctivitis, ocular rosacea, retinal vasculitis, bullous pemphigoid, mucous membrane pemphigoid, Sjogren's syndrome, episcleritis, scleritis, uveitis, optic neuritis, ischemic optic neuropathy, pain, dry eye, macular degeneration, diabetic retinopathy, herpes simplex keratitis, or endophthalmitis.

Also provided is a topical pharmaceutical composition for treating oropharyngeal dysphagia. The composition includes a cannabinoid and pharmaceutically acceptable excipients, wherein the composition provides a dose of cannabinoid from 0.1 mg to 20 mg.

The details of one or more embodiments are set forth in the description and the examples below. Other features, objects, and advantages will be apparent from the detailed description of several embodiments and also from the claims.

DETAILED DESCRIPTION

An innovative cranial drug delivery route is disclosed in which topical, nasal, intradermal, or subcutaneous drug delivery innervate cranial nerves, e.g., the trigeminal and the facial nerves, providing a novel modality for treatment and potential cure of diseases and conditions that cannot be treated easily via the vascular system. The topical composition can contain the active drug in concentrations from about 0.01% by weight to about 80% by weight. Any of the pharmaceuticals described below can be formulated with appropriate excipients known in the art. The formulation can be, e.g., a liquid or semi-solid, a solution, a suspension, an emulsion, a gel, a cream, a lotion, an ointment, or a patch. Delivery can be simple or actively assisted by an electric current or other electrophysical device. The pharmaceutical can be administered by applying it to the forehead. In an alternative embodiment, the pharmaceutical can be administered by iontophoresis or by subcutaneous or intradermal injection to the forehead.

The composition of the present invention can be applied topically to the face to the regions that are outside of the palpebral part of the eye. The palpebral part of the eye refers to the region of and around the eye associated with the palpebral component of the orbicularis oculi muscle group. The palpebral component of the muscles originates in the palpebral ligament and runs above and below the eye to the lateral angle of the eye, forming concentric circles around the eye. The palpebral part of the eye thus refers to the facial surface around the eye that corresponds to the location of the palpebral component of the orbicularis oculi muscle lying underneath the facial skin. Non-limiting examples of these regions include, for example, the forehead above the eyebrows, the temple area between the end of the eyebrow and the hairline including the temple region, the upper cheek, or the sides or bridge of the nose. In one embodiment, the composition of the present invention is applied to the forehead. In another embodiment, the composition is applied to one or both temple regions. In a further embodiment, the composition is applied to the upper cheek. In another embodiment, the composition is applied to one or both sides or the bridge of the nose. In one embodiment, the composition is applied to two or more regions of the face simultaneously or sequentially, and proximately or distant in time. For example, the composition can be applied to the forehead, and further applied to the temple region at the same time or at the next prescribed time, whether such next prescribed time is the same day or a different day. In one embodiment, the composition is applied to the same region of the face each time it is applied. In another embodiment, the composition is applied to any area of the skull, exclusive of the palpebral part of the eye. In a further embodiment, the composition can be applied intranasally to the mucous membrane inside of the nose.

Not to be bound by theory, it is believed that topical application of a pharmaceutical or other compound to the forehead and temple areas results in rapid delivery and/or action, i.e., within less than 10 minutes, via a cranial nerve, including cranial nerve V (trigeminal nerve), VII (facial nerve), I, II, III, IV, VI, VIII, IX, X, XI, and XII, or rapid entry into the microcirculation of the vascular system. It is also believed that the rapid action of drugs delivered cranially can be attributed to drug absorption of the drug through the skin of the forehead, uptake by receptors residing in nerve endings in the skin and induction of signaling in the brain. The brain can then respond to the drug by sending appropriate signals to target muscles, glands, and organs. A drug delivered to a cranial nerve can exert its effect on an organ or gland that is innervated by that nerve. Another advantage of this drug delivery route is evidenced by the observation that nerves damaged, extirpated, or infected by a virus, e.g., a neurotropic virus, can be treated by the method described above. Additionally, a much lower dose of active drug, as compared to the dose required for systemic delivery, can be effective, thereby enhancing safety.

The cranial drug delivery method can be used advantageously to treat diseases and conditions including but not limited to CNS diseases such as traumatic brain injury and neurodegenerative diseases, pain, especially neuropathic pain that cannot be treated effectively with current pain drugs, eye diseases and conditions, and infections due to neurotrophic microbes. Microbe as used here refers to a virus, a bacteria, a fungus, or a mold. The method is particularly effective when practiced on a mammal, including but not limited to dogs and humans.

Among the advantages of the disclosed cranial drug delivery method as compared to typical methods is that a lower dose of drug is required to produce a therapeutic effect, thereby minimizing side effects. It has also been found that a dose of a drug ineffective when administered systemically is effective if applied cranially. The delivery route is convenient, allowing administration to people who cannot take oral drugs. It is also less cumbersome than injectables and can be accurately dosed. Drugs administered by cranial delivery are faster acting, rendering drug half-life less relevant as compared to systemic administration. The method also renders unnecessary intravitreous injections which are painful and risky.

The cranial delivery method also allows for greater flexibility in administering drug combinations. For example, two drugs that are typically taken at different times of day can be administered simultaneously via the cranial delivery method. More specifically, a drug that must be taken on an empty stomach can be co-administered with a drug that must be taken after a meal. Additionally, multi-drug regimens can be simplified by administering all drugs together cranially. For example, many elderly patients who are prescribed multiple medications forget to take one or more of the medications as directed. The cranial delivery method can be used to deliver a combination of the prescribed medications in a single application, thus avoiding accidental non-compliance. Drug mix-ups can also be avoided by providing a single combination of medication. Cranial delivery can also avoid drug irritation issues, e.g., gastric distress, associated with typical delivery methods.

The cranial delivery method, as mentioned above, has the advantage of delivering drugs rapidly and simultaneously. This advantage can be exploited for treating addiction or for tapering drug doses. For example, a patient on high dose dexamethasone therapy often cannot be withdrawn from that medication without suffering serious side effects at lower doses. Tapered doses of dexamethasone can be applied cranially together with increasing doses of hydrocortisone to alleviate the effects of tapering. In another example, an individual addicted to a drug, e.g., an opiate, can be administered diminishing doses of buprenorphine cranially until complete withdrawal is accomplished.

Many difficult to treat or previously untreatable conditions can advantageously be treated by the method described herein.

For example, progesterone or progestins can be administered cranially to control pain, inflammation, and bruising. Progesterone can also be delivered by the cranial method to treat dry eyes. Progesterone can also lessen discomfort, redness, and irritation associated with contact lens wear. Cranially administered progesterone can prevent or reduce the risk of cellular damage and the development of dry eye resulting from wearing contact lenses. The effects of progesterone also allow a contact lens wearer to increase the duration of contact lens wear.

Progesterone can be delivered by the cranial method to stimulate eyelash and eyebrow growth for aesthetic purposes and for treating madarosis, i.e., the loss of eyebrows or eyelashes associated with a medical condition or a drug treatment.

Madarosis can be scarring or non-scarring depending upon the etiology. Scarring madarosis is typically treated by follicular unit transplantation. Cranial application of a topical progesterone composition can lessen or eliminate the need for such surgical intervention.

Conditions associated with madarosis include, but are not limited to, atopic dermatitis, seborrhoeic dermatitis, lamellar ichthyosis, psoriasis, frontal fibrosing alopecia, ulerythema ophryogenes, acne rosacea, telogen effluvium, follicular mucinosis, cutaneous sarcoidosis, alopecia areata, discoid lupus erythematosus, en coup de sabre, Graham-Little syndrome, Parry-Romberg syndrome, Vogt Koyanagi Harada syndrome, leprosy, secondary syphilis, viral infections, fungal infections, demodicosis, phthiriasis palpebrarum, trichotillomania, tumors, systemic mastocytosis, cutaneous T-cell lymphoma, and trichodysplasia spinulosa.

Madarosis also results from radiotherapy for ocular tumors, cocaine abuse, drug treatment (e.g., retinoids, heparin, anticonvulsants, angiotensin-converting enzyme inhibitors, androgens, miotics, anticoagulants, anti-cholesterol drugs, antithyroid drugs, propranolol, valproic acid, boric acid, bromocriptine, and chemotherapeutic drugs), hypervitaminosis A, thallium poisoning, and mercury poisoning.

Progesterone, estradiol, and testosterone can be delivered by the method described above to effect hormone replacement therapy. Hormone replacement therapy by cranial administration of these hormones can advantageously be carried out using much lower doses of hormone than is typically prescribed and positive results are achieved in a shorter time. Progesterone or testosterone can be delivered by the method for treating erectile dysfunction. Progesterone, estradiol, and testosterone can be delivered by the method described above for management of transgender conditions. Cranial application of progesterone can improve surface eye disease, i.e. corneal lesions and thinning as a result of herpetic keratitis, and can also be used for treating trigeminal neuralgia. Additionally, cranially-delivered progesterone can be effective for treating symptoms resulting from dyslexia including, but not limited to, decreased visual acuity, poor reading fluency, difficulty in reading aloud, headlight glare during evening driving Progesterone delivered cranially can also vastly improve symptoms of traumatic brain injury. The precursor of progesterone, pregnenolone, or the metabolites such as allopregnanoline and pregnanolone can also be similarly applied cranially for treating the above-mentioned diseases or conditions.

The antiviral drug ganciclovir applied cranially can be used for treating ocular or facial herpes zoster or HSV-1, either active or subclinical. Cranial shingles and HSV-1 can also be treated with cranially applied ganciclovir, penciclovir, or acyclovir.

Additionally, a cannabinoid, e.g., a delta-9-tetrahydrocannabinol, which can be (6aR-trans)-6a,7,8,10a-tetrahydro-6,6,9-trimethyl-3-pentyl-6H-dibenzo[b,d]pyran-1-ol ("dronabinol"), delivered cranially can be used for treating anorexia induced by chemotherapy, for treating nausea, and can block the induction of anorexia by antidepressants. Dronabinol can also be used to elevate blood pressure by applying it to the forehead.

In a particular embodiment, dronabinol can be used to treat oropharyngeal dysphagia. The oropharyngeal dysphagia that can be treated may result from the following: (i) iatrogenic causes (e.g., side effects of medication, chemotherapy, neuroleptics, postsurgical muscular or neurogenic causes, and radiation); (ii) infectious (e.g., diphtheria, botulism, Lyme disease, syphilis, polio, postpolio syndrome, herpes, cytolomegalovirus, and candida); (iii) metabolic (e.g., amyloidosis, Cushing's syndrome, thyrotoxicosis, and Wilson's disease); (iv) myopathic: (e.g., connective tissue disease, (overlap syndrome, dermatomyositis, myasthenia gravis, myotonic dystrophy, oculopharyngeal dystrophy, polymyositis, sarcoidosis, and paraneoplastic syndromes); and (v) neurological (e.g., brainstem tumors, head trauma, stroke, cerebral palsy, Guillain-Barre syndrome, Huntington's disease, multiple sclerosis, tardive dyskinesia, metabolic encephalopathies, amyotrophic lateral sclerosis, Parkinson's disease, and dementia).

Dronabinol delivered cranially to an individual with dementia, e.g., Alzheimer's disease, can also alleviate anxiety agitation, aggressive behavior, nocturnal restlessness and disorientation, wandering, disorientation, delusions, depression, and insomnia, among other symptoms.

As mentioned above, topical compositions for cranial application can contain the active drug in concentrations from about 0.01% by weight to about 80% by weight. For example, the concentration of active drug can be 0.01%, 0.05%, 0.1%, 0.25%, 0.5%, 1%, 2.5%, 5%, 10%, 20%, 25%, 50%, 75%, and 80%. The dose of an active drug that can be applied by this method can range from 0.01 mg to 100 mg. For example, the dose of active drug applied can be 0.01 mg 0.05 mg, 0.1 mg, 0.25 mg, 0.5 mg, 1 mg, 2 mg, 2.5 mg, 5 mg, 10 mg, 20 mg, 25 mg, 50 mg, 75 mg, 80 mg, 90 mg, and 100 mg.

In one embodiment, a topical ganciclovir composition can be applied at a concentration of 0.05-2% by weight of the composition, at a dose of 0.05 to 2 mg two to four times a day. For example, 0.15 mg per application can be administered cranially four times daily.

In another embodiment, a 0.1% to 20% by weight formulation of progesterone can be applied cranially at a dose of 0.1 to 20 mg progesterone. For example, 0.25% to 1% progesterone (e.g., 0.25 mg to 1 mg) can be applied topically to the forehead as described above. In another example, application to the forehead of low dose progesterone gel (0.25% to 1%) effectively increases the length, strength, density, thickness, and curl of eyelashes, and darkens their appearance over a pre-treatment baseline.

The topical cranial drug delivery method of this invention can be used to treat facial palsies caused by infections, including Bell's palsy. Infections can also be treated, including but not limited to external otitis, otitis media, mastoiditis, chickenpox, diphtheria, Herpes zoster cephalicus (Ramsey Hunt syndrome), encephalitis, poliomyelitis (type 1), mumps, mononucleosis, leprosy, influenza, coxsackievirus, malaria, syphilis, tetanus, tuberculosis, botulism, acute hemorrhagic conjunctivitis (enterovirus 70), gnathostomiasis, mucormycosis, Lyme disease, cat scratch, and HIV.

Craniofacial pain can also be treated by the above described cranial administration method. The following non-limiting examples can be treated by the method of the invention. Anesthesia dolorosa, central post-stroke pain, facial pain attributed to multiple sclerosis, persistent idiopathic facial pain, burning mouth syndrome, glossopharyngeal neuralgia, nervus intermedius neuralgia, occipital neuralgia, postherpetic neuralgia, raeder paratrigeminal syndrome, superior laryngeal neuralgia, trigeminal neuralgia, cluster-tic syndrome, cancer pain, dental pain, giant cell arteritis, posttraumatic and postoperative pain, primary headache, and temporomandibular joint syndrome, The cranial delivery method can also be used for treating ophthalmic diseases, including but not limited to glaucoma, allergic conjunctivitis, ocular rosacea, retinal vasculitis, bullous pemphigoid, mucous membrane pemphigoid, Sjogren's syndrome, episcleritis, scleritis, uveitis, optic neuritis, ischemic optic neuropathy, pain, dry eye, macular degeneration, diabetic retinopathy, herpes simplex keratitis, or endophthalmitis.

Cranial delivery of progesterone is effective for treating eye discomfort resulting from iatrogenic causes, including but not limited to medication use (e.g., anti-histamines, glaucoma medication, immunosuppressants such as cyclosporine), and surgical procedures (e.g., laser eye surgery, cataract operations, and corneal transplants).

Progesterone applied cranially is effective for treating ocular tissue damage, such as epithelial defects, ocular allergy such as those caused by seasonal, perennial, animal, insect, or other environmental allergens, and ocular redness that can be conjunctival, caused by eye strain or irritation.

As mentioned above, cranial delivery can allow a drug to reach an area of the body that cannot be reached by other means of administration, such as behind the eye. Thus, within the scope of this invention is combination therapy with at least two drugs, one administered cranially and one administered directly to the front of the eye. For example, progesterone, ganciclovir, or both can be administered cranially concomitant with an antibiotic administered to the front of the eye for treating ophthalmic diseases.

Acquired neurodegenerative diseases can also be treated by the method described supra. For example, the method can be used for treating amyotrophic lateral sclerosis (ALS), progressive supranuclear palsy (PSP), Parkinson's disease, multiple system atrophy, corticobasal degeneration (CBD), Alzheimer's disease, dementia with Lewy bodies, frontotemporal dementia, and poststroke dementia.

Also treatable by cranial drug delivery are acquired immune or inflammatory disorders, such as peripheral neuropathy associated with infection by Borellia burgdorferi (Lyme disease), Chagas disease, leprosy (Hansen's disease), rabies virus, inflammatory neuropathies, Guillain-Bane syndrome (GBS), chronic inflammatory, demyelinating polyneuropathy (CIDP), Sjogren's syndrome, systemic lupus erythematosus, and multiple sclerosis.

Certain embodiments are set out below.

Disclosed is the use of a topical progesterone composition for treating contact lens discomfort, eye discomfort resulting from iatrogenic causes, ocular allergy, ocular tissue damage, ocular redness, inflammatory conditions of the eye, blepharitis, meibomian cyst, uveitis, punctate keratitis, retinitis, dyslexia, pain, neuralgia, blepharospasm, and facial palsy, wherein the composition is administered to an area of the face not including the palpebral part of the eye. The area of the face not including the palpebral part of the eye can be the forehead, the temple region, the upper cheek, or the bridge of the nose.

Also disclosed is the use of a topical progesterone composition for stimulating eyelash and eyebrow growth, wherein the composition is administered to an area of the face not including the palpebral part of the eye. The area of the face not including the palpebral part of the eye can be the forehead, the temple region, the upper cheek, or the bridge of the nose.

Further disclosed is the use of a topical cannabinoid composition for reducing behavioral and psychological symptoms associated with dementia and for treating surgically-induced cognitive and speech defects, cerebral palsy, anorexia, nausea, and oropharyngeal dysphagia, wherein the composition is administered to an area of the face not including the palpebral part of the eye. The area of the face not including the palpebral part of the eye can be the forehead, the temple region, the upper cheek, or the bridge of the nose. A dose of cannabinoid from 0.1 mg to 20 mg can be administered. The cannabinoid can be dronabinol. The oropharyngeal dysphagia can be caused by an injury, an infection, a metabolic condition, an autoimmune condition, a neurological condition, a structural defect, or a medical treatment.

Also provided is the use of a topical anxiolytic composition for relieving anxiety, wherein the composition is administered to an area of the face not including the palpebral part of the eye.

Further provided is the use of an antimicrobial agent for treating a disease or condition mediated by a neurotropic microbe, wherein the composition is administered to an area of the face not including the palpebral part of the eye. The area of the face not including the palpebral part of the eye can be the forehead, the temple region, the upper cheek, or the bridge of the nose. The neurotropic microbe can be a neurotropic virus and the antimicrobial agent can be ganciclovir, acyclovir, valganciclovir, ribavirin, famciclovir, oseltamavir, docosanol, penciclovir, cidofovir, rimantadine, zanamivir, or foscarnet. The condition mediated by a neurotropic microbe can be a surface ocular disease. The neurotropic microbe can be Varicella zoster or Herpes simplex. The disease mediated by a neurotropic microbe can be herpetic keratitis.

Additionally provided is a method for treating an ophthalmic disease or condition, the method comprising: identifying a subject having the disease or condition, and administering topically a topical progesterone composition to an area of the face of the subject not including the palpebral part of the eye, wherein the ophthalmic disease or condition is selected from the group consisting of contact lens discomfort, ocular allergy, ocular tissue damage, ocular redness, allergic conjunctivitis, corneal damage, eye discomfort resulting from eye surgery or ocular medication, blepharitis, meibomian cyst, uveitis, punctate keratitis, retinitis, vision problems associated with dyslexia, corneal lesions and thinning resulting from herpetic keratitis, shortened and sparse eyelashes and eyebrows, glaucoma, ocular rosacea, retinal vasculitis, bullous pemphigoid, mucous membrane pemphigoid, Sjogren's syndrome, episcleritis, scleritis, optic neuritis, ischemic optic neuropathy, ocular pain, macular degeneration, diabetic retinopathy, herpes simplex keratitis, and endophthalmitis.

Also disclosed is the use of progesterone for the manufacture of a topical medicament for administering topically to an area of the face of a subject not including the palpebral part of the eye for treating an ophthalmic disease or condition selected from the group consisting of contact lens discomfort, ocular allergy, ocular tissue damage, ocular redness, allergic conjunctivitis, corneal damage, eye discomfort resulting from eye surgery or ocular medication, blepharitis, meibomian cyst, uveitis, punctate keratitis, retinitis, vision problems associated with dyslexia, corneal lesions and thinning resulting from herpetic keratitis, shortened and sparse eyelashes and eyebrows, glaucoma, ocular rosacea, retinal vasculitis, bullous pemphigoid, mucous membrane pemphigoid, Sjogren's syndrome, episcleritis, scleritis, optic neuritis, ischemic optic neuropathy, ocular pain, macular degeneration, diabetic retinopathy, herpes simplex keratitis, and endophthalmitis.

Further provided is a method for treating oropharyngeal dysphagia, the method comprising: identifying a subject having oropharyngeal dysphagia, and administering topically a topical cannabinoid composition to an area of the face the subject not including the palpebral part of the eye. The oropharyngeal dysphagia is associated with side effects of medication, neuroleptics, postsurgical muscular or neurogenic causes, radiation, diphtheria, botulism, Lyme disease, syphilis, polio, postpolio syndrome, herpes, cytolomegalovirus, candida, amyloidosis, Cushing's syndrome, thyrotoxicosis, Wilson's disease, overlap syndrome, dermatomyositis, myasthenia gravis, myotonic dystrophy, oculopharyngeal dystrophy, polymyositis, sarcoidosis, paraneoplastic syndrome, brainstem tumors, head trauma, stroke, cerebral palsy, Guillain-Barre syndrome, Huntington's disease, multiple sclerosis, tardive dyskinesia, metabolic encephalopathies, amyotrophic lateral sclerosis, Parkinson's disease, achalasia, or dementia.

Additionally provided is the use of a cannabinoid for the manufacture of a topical medicament for administering topically to an area of the face of a subject not including the palpebral part of the eye for treating oropharyngeal dysphagia.

Cranial Delivery of Psychoactive Compounds

Topical administration to the forehead is a novel and convenient way to deliver pharmaceutical compounds that act on the central nervous system. These include, e.g., stimulants, antipsychotics, anxiolytics, benzodiazepines, antidepressants, anti-narcoleptics, muscle relaxants, anticonvulsants, analgesics. Other pharmaceuticals that can be delivered by this method include, but are not limited to, those pharmaceuticals for treating for bipolar disorder, insomnia, dementia, fibromyalgia, multiple sclerosis, neuromuscular disorders, Parkinson's disease, attention deficit hyperactivity disorder (ADHD), narcolepsy, Alzheimer's disease, seizure disorders. A more complete list is shown in Table 1 below.

TABLE 1

Neuroactive drugs that can be administered topically to the forehead grouped by drug type or medical conditions.

| | |
|---|---|
| ADHD | Fluphenazine |
| Dextroamphetamine | Haloperidol |
| Amphetamine | Perphenazine |
| Methylphenidate | Trifluoperazine |
| Dexmethylphenidate | Loxapine |
| Atomoxetine | Pimozide |
| Guanfacine | Thioridazine |
| Lisdexamfetamine | Thiothixene |
| Clonidine | Antipsychotics, 2nd Generation |
| Methamphetamine | Aripiprazole |
| Antipsychotics, 1st Generation | Clozapine |
| Chlorpromazine | Olanzapine |
| | Quetiapine |
| Risperidone | Clomipramine |
| Paliperidone | Desipramine |
| Ziprasidone | Doxepin |
| Iloperidone | Imipramine |
| Asenapine | Nortriptyline |
| Anxiolytics | Protriptyline |
| Buspirone | Trimipramine |
| Hydroxyzine | |
| Meprobamate | Other Antidepressants |
| Benzodiazepines, Short Acting | Bupropion |
| Alprazolam | Mirtazapine |
| Midazolam | Trazodone |
| Oxazepam | Nefazodone |
| Benzodiazepines, Mid-Acting | Vilazodone |
| Lorazepam | Narcolepsy |
| Benzodiazepines, Long-Acting | Modafinil |
| Chlordiazepoxide | Armodafinil |
| Diazepam | Caffeine |
| Clorazepate | Other |
| Bipolar Disorder | Lurasidone |
| Aripiprazole | Maprotiline |
| Carbamazepine | Neurological Disorders |
| Lithium | Alzeheimer's disease/Dementias |
| Olanzapine | Donepezil |
| Insomnia | Memantine |
| Hydroxyzine | Rivastigmine |
| Lorazepam | Galantamine |
| Doxepin | Fibromyalgia |
| Monoamine Oxidase Inhibitors | Milnacipran |
| Phenelzine | Pregabalin |
| Selegiline | Fosphenytoin |
| Tranylcypromine | Multiple Sclerosis |
| Serotonin-norepinephrine reuptake inhibitors | Glatiramer |
| | Neuromuscular Disorders |
| Duloxetine | Pyridostigmine |
| Venlafaxine | Hydroxide |
| Desvenlafaxine | Neostigmine |
| Selective Serotonin Reuptake Inhibitors | Riluzole |
| | Parkinson's Disease |
| Citalopram | Carbamazepine |
| Escitalopram | Carbidopa |
| Fluoxetine | Levodopa |
| Paroxetine | Apomorphine |
| Sertraline | Bromocriptine |
| Fluvoxamine | Pramipexole |
| Vilazodone | Rotigotine |
| Tricyclic Antidepressants | Ropinirole |
| Amitriptyline | Selegiline |
| Seizure Disorders | Fentanyl |
| Rufinamide | Hydrocodone |
| Divalproex | Hydromorphone |
| Phenytoin | Levorphanol |

TABLE 1-continued

Neuroactive drugs that can be administered topically to the forehead grouped by drug type or medical conditions.

| | |
|---|---|
| Levetiracetam | Meperidine |
| Lamotrigine | Methadone |
| Vigabatrin | Morphine |
| Ethosuximide | Nalbuphine |
| Primidone | Oxycodone |
| Valproic Acid | Oxymorphone |
| Topiramate | Pentazocine |
| Lacosamide | Tapentadol |
| Zonisamide | Tramadol |
| Gabapentin | Opium |
| Felbamate | Propoxyphene |
| Tiagabine | Other Analgesics |
| Oxcarbazepine | Rizatriptan |
| Other | Eletriptan |
| Tetrabenazine | Zolmitriptan |
| Gabapentin Enacarbil | Butalbital |
| Entacapone | Diphenhydramine |
| Rasagiline | Frovatriptan |
| Fampridine | Almotriptan |
| Botulinum A Toxin | Dihydroergotamine |
| Benztropine | Naratriptan |
| Amantadine | Naloxone |
| Dextromethorphan | Naltrexone |
| Quinidine | Salsalate |
| Tolcapone | Diflunisal |
| Botulism Antitoxin B | Ergotamine |
| Trihexyphenidyl | Isometheptene |
| Methsuximide | Phenyltoloxamine |
| Ethotoin | Clonidine |
| Capsaicin | Menthol |
| Procyclidine | Camphor |
| Physostigmine | Pamabrom |
| Dexpanthenol | Meprobamate |
| Ambenonium | Methapyrilene |
| Guanidine | Phenobarbital |
| Bethanechol | Phenylephrine |
| | Promethazine |
| Analgesics | Sumatriptan |
| Opioids | Muscle Relaxants |
| Buprenorphine | Cyclobenzaprine |
| Butorphanol | Carisoprodol |
| Codeine | Dantrolene |
| Codeine | Baclofen |
| Dihydrocodeine | Chlorzoxazone |
| Chlorzoxazone | Methyltestosterone |
| Orphenadrine | Mometasone |
| Methocarbamol | Diflorasone |
| Tizanidine | Lanreotide |
| Zoledronic Acid | Fludrocortisone |
| Raloxifene | Oxandrolone |
| Teriparatide | Flurandrenolide |
| Metaxalone | Tesamorelin Acetate |
| Cisatracurium | Halobetasol |
| Colecalciferol | Mecasermin |
| Rocuronium | Levonorgestrel |
| Quinine | Hydroxyprogesterone |
| Vecuronium | Clocortolone |
| Succinylcholine | Drospirenone |
| Pamidronic Acid | Halcinonide |
| Atracurium | Vasopressin |
| Caffeine | Oxytocin |
| Etidronic Acid | Methylergonovine |
| Ergocalciferol | Danazol |
| Pancuronium | Clomiphene |
| Tiludronate | Alclometasone |
| Phenyltoloxamine | Cetrorelix |
| Hormones | Norgestimate |
| Testosterone | Nafarelin |
| Somatropin | Oxymetholone |
| Estrogenic Sub, Conjugated | Estropipate |
| Estradiol | Triamcinolone Hexacetonide |
| Betamethasone | Amcinonide |
| Clobetasol | Fluoxymesterone |
| Methylprednisolone | Cortisone |
| Hydrocortisone | |
| Triamcinolone Acetonide | Antiviral Agents with Efficacy for Head and Neck and CNS |
| Progesterone | |

TABLE 1-continued

Neuroactive drugs that can be administered topically to the forehead grouped by drug type or medical conditions.

| | |
|---|---|
| Medroxyprogesterone | Valacyclovir |
| Norethindrone | Acyclovir |
| Calcipotriene | Valganciclovir |
| Desmopressin | Ribavirin |
| Desoximetasone | Famciclovir |
| Desonide | Oseltamavir |
| Fluocinonide | Docosanol |
| Dinoprostone | Penciclovir |
| Dexamethasone | Ganciclovir |
| Prednisolone | Cidofovir |
| Fluticasone | Rimantadine |
| Ethinylestradiol | Zanamivir |
| Corticotrophin | Foscarnet |
| Prednisone | Anti-Infectives With Efficacy For Head And Neck And CNS |
| Fluocinolone Acetonide | |
| Minocycline | Betaxolol |
| Doxycycline | Levobunolol |
| Vancomycin | Carteolol |
| Azithromycin | Alpha-1 Agonist and Partial Alpha-2 Agonist |
| Clindamycin | |
| Meropenem | Oxymetazoline |
| Ceftriaxone | Steroids |
| Clarithromycin | Dexamethasone |
| Cefepime | Loteprednol Etabonate |
| Erythromycin | Prednisolone |
| Cefpodoxime | Hydrocortisone |
| Proxetil | Fluorometholone |
| Metronidazole | Difluprednate |
| Amikacin | Rimeloxone |
| Tetracycline | Fluocinolone Acetonide |
| Antifungals With Efficacy For Head And Neck And CNS | Triamcinolone Acetonide |
| Voriconazole | Carbonic Anhydrase Inhibitors |
| Micafungin | Dorzolamide |
| Amphotericin B | Brinzolamide |
| Itraconazole | Acetazolamide |
| Ketoconazole | |
| Caspofungin | NSAIDs |
| Posaconazole | Bromfenac |
| Fluconazole | Nepafenac |
| Flucytosine | Flurbiprofen |
| Immunologic Agents | Ketorolac |
| Tacrolimus | Diclofenac |
| Lenalidomide | Macular Degeneration |
| Sirolimus | Verteporfin |
| Thalidomide | Anesthetics |
| Cyclosporine | Proparacaine |
| Everolimus | Tetracaine |
| Ophthalmic Preparations | Lidocaine |
| Prostaglandins | Anticholinergics |
| Travoprost | Tropicamide |
| Bimatoprost | Homatropine |
| Latanoprost | Glaucoma Agents |
| Calcineurin Inhibitor | Carbachol |
| Cyclosporine | Ecothiopate Methazolamide |
| Alpha-Adrenergic Agonists | Mast Cell Stabilizers |
| Brimonidine | Nedocromil |
| Apraclonidine | Lodoxamide |
| Phenylephrine | Cromolyn |
| Beta Blockers | Pemirolast |
| Timolol | Potassium |
| Metipranolol | Other |
| Scopolamine | Ingredient |
| Pilocarpine | Sedatives and Hypnotics |
| Acetylcholine | Zolpidem |
| Hydroxide | Eszopiclone |
| Anti-VEGF | Temazepam |
| Pegaptanib | Ramelteon |
| Sympathomimetic Drug | Pentobarbital |
| Hydroxyamphetamine | Phenobarbital |
| Anti-infectives Other Than Antiviral | Doxepin |
| Moxifloxacin | Zaleplon |
| Tobramycin | Diphenhydramine |
| Gatifloxacin | Doxylamine |
| Polymyxin B | Triazolam |
| Erythromycin | Methylphenobarbital |
| Azithromycin | Secobarbital |
| Neomycin | Melatonin |
| Bacitracin | Estazolam |
| Gentamicin | Chloral Hydrate |
| Ganciclovir | Butabarbital |
| Ofloxacin | Flurazepam |
| Besifloxacin | Amobarbital |
| Trimethoprim | Methapyrilene |
| Sulfacetamide | Scopolamine N-Oxide |
| Ciprofloxacin | Dimenhydrinate |
| Trifluridine | Quazepam |
| Levofloxacin | Scopolamine |
| Gramicidin | Cardiac Agents |
| Natamycin | Epinephrine |
| Oxytetracycline | Ranolazine |
| Antihistamines | Dronedarone |
| Bepotastine | Nitroglycerin |
| Azelastine | Propafenone |
| Pheniramine | Isosorbide-5-Mononitrate |
| Epinastine | |
| Alcaftadine | Digoxin |
| Ketotifen | Nesiritide |
| Emedastine | Amiodarone |
| Olopatadine | Midodrine |
| Antazoline | Isosorbide Dinitrate |
| Dipivefrine | Flecainide |
| | Sotalol |
| Sexual Function Disorder | Milrinone |
| Sildenafil | Indomethacin |
| Tadalafil | Hydralazine |
| Vardenafil | Dofetilide |
| Alprostadil | Disopyramide |
| Benzocaine | Dobutamine |
| Non Pharmaceutical | Dopamine |
| Isoproterenol | Varenicline |
| Procainamide | Nicotine |
| Quinidine | Bupropion |
| Ibutilide | Nikethamide |
| Mexiletine | Cough/Cold/Flu Preparations |
| Amyl Nitrite | Dextromethorphan |
| Ubiquinones | Chlorpheniramine |
| Amrinone | Guaifenesin |
| Moricizine | Phenylephrine |
| Antinauseant | Pseudoephedrine |
| Palonosetron | Doxylamine |
| Fosaprepitant | Brompheniramine |
| Dronabinol | Homatropine |
| Ondansetron | Promethazine |
| Aprepitant | Benzonatate |
| Scopolamine | Carbetapentane |
| Promethazine | Pyrilamine |
| Meclizine | Diphenhydramine |
| Granisetron | Chlophedianol |
| Prochlorperazine | Dexchlorpheniramine |
| Trimethobenzamide | Ephedrine |
| Dimenhydrinate | Guaiacolsulfonate |
| Dolasetron | Chlorcyclizine |
| Nabilone | Dexbrompheniramine |
| Cyclizine | Clofedanol Noscapine |
| Thyroid Therapy | Pheniramine |
| Levothyroxine | Triprolidine |
| Liothyronine | Bromodiphenhydramine |
| Methimazole | Carbinoxamine |
| Propylthiouracil | Methscopolamine |
| Smoking Deterrents | Phenindamine |

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference.

Example 1: Treatment of Drug-Induced Anorexia and Oropharyngeal Dysphagia

A patient had been on dexamethasone therapy for 20 months following surgery, radiation, and chemotherapy. After tapering the dose of dexamethasone from 16 mg per day to 1.5 mg per day, the patient was unable to swallow and reported a loss of appetite. Dronabinol was administered to the patient's forehead once per day at 2.5 mg per dose. Improvement in swallowing and appetite were noted within 24 hours of the first administration. The patient reported a healthy appetite and no problems swallowing after four weeks of topically applied dronabinol.

After missing one day of dronabinol therapy, the patient reported a decrease in appetite and difficulty swallowing liquids. Restoration of cranial dronabinol therapy resulted in a normal appetite and swallowing after one day. After three weeks of continued dronabinol therapy, application was again stopped for 24 hours, resulting in the same loss of appetite and difficulty swallowing. The patient reported a complete reversal of symptoms within about two hours after a single dose of dronabinol to his forehead.

The effect of oral administration of dronabinol was tested after another two weeks as an alternative to the topical route of administration described above. Within one day after starting oral administration of 2.5 mg dronabinol, the patient had difficulty swallowing and chewing. Patient was rescued again by single dose applied cranially and is currently eating normally and chewing and swallowing. Typical meals include steak, meatball sandwich and fruit drinks.

Continued treatment after one year including multiple challenge stops and restarts of cranial drug dosing confirms that daily dosing is necessary for continued effectiveness. No increase in dose has been required. The patient had also ceased dexamethasone dosing very early on.

Example 2: Treatment of Surgically Induced Cognitive Deficits

The patient described in Example 1 suffered from a co-morbid condition of cognitive impairment due to surgery to remove a frontal lobe glioblastoma multiforma. The cognitive impairment continued for two years following the surgery at which time treatment with cranially delivered dronabinol was begun. The patient's physicians have noted, since cranially delivered dronabinol therapy was initiated, a dramatic improvement in cognitive function, as well as a noticeable decrease in scar tissue around the area of surgery as detected by imaging.

Example 3: Treatment of Trigeminal Neuralgia and Facial Palsy

A subject presented with left-side trigeminal neuralgia and left side facial droop of 10 years duration.

Therapy was initiated by topically applying progesterone (1% by weight) equivalent to 1 mg four times daily to the patient's forehead. This was followed by application of 0.15 g ganciclovir (as a 0.15% by weight formulation) up to five times daily.

The treatment resulted in relaxation of facial muscles that had been contracted for 10 years after a herpes virus infection.

Example 4: Treatment of Herpetic Keratitis

A 67 year old male suffered a first onset of active corneal Herpes zoster at age 56. He presented with classic Herpes Zoster symptoms including, left hemisphere unilateral skin lesions on forehead, bridge of nose area and down the nose not including the tip; left cornea dendrites, keratitis and edema; loss of functional vision, elevated intraocular pressure as high as 42 mm Hg, conjunctival irritation and redness and anesthetic cornea. There were also general body flu symptoms. The individual had a history of childhood chickenpox and mononucleosis.

The patient was initially treated with ophthalmic prednisolone acetate 1% up to 5 times daily, ophthalmic antibiotics, non-prescription ophthalmic wetting agents, and lubrication with gels administered to the eye. Additional drug therapies included systemic oral valcyclovir as high as 2 g per day and medications to reduce intraocular pressure.

The treatment regimen did not result in any return of functional vision. Despite the therapy, symptom flare-up was as frequent as 2 weeks to 1 month over the past 10 years. Although intraocular pressure returned to within the normal range, cataracts formed as a result of long term use of corticosteroids.

The cornea began to demonstrate surface thinning with a loss of epithelial cells. The cornea surface contour became increasingly distorted with prominent ridges. There was incursion of capillaries across the conjunctiva into the cornea, both superficially and deep. Deposition of phospholipids through a leaching process occluded the cornea with grey color deposits on about 50% of its surface.

An ophthalmological exam revealed edema and large areas of phospholipid deposits. Corneal thinning had progressed to near perforation levels which required preparation for corneal patch surgery.

At this point, 1% topical progesterone (approximately 1 mg of progesterone) was first administered as a method to keep the cornea from perforating and the tear film intact. The drug was applied to the forehead 4 times daily together with topical antibiotics and corticosteroids. Further corneal deterioration was halted and gradually all other medications other than the topical progesterone were stopped. During a one year period of treatment 2 or 3 times a day with 1 mg progesterone to the forehead and no other drugs, the cornea remained unperforated.

After stabilizing the cornea, antiviral treatment was begun with ganciclovir gel (0.15%; 0.15 mg of drug) applied five times. daily to the forehead together with once daily progesterone (1%; 1 mg of drug) and a nightly drop of ophthalmic antibiotic. Intraocular pressure measured at the onset of ganciclovir treatment was 18 mm Hg.

The patient reported a decrease in eye strain as a result of an improvement in tear film. After 1 week of treatment with the two drugs, there was less inflammation and a slight improvement in visual acuity in particular in high contrast fields of view to close on object. Over the next two weeks, inflammation was further reduced and visual acuity increased somewhat when the head was tilted back. During the first full month of treatment, the affected eye generally felt comfortable. There was a lack of inflammation, and some vision returned to the threshold of functionality. Intraocular pressure remained normal in the range of 16 mm Hg.

An examination revealed that the particular area was in fact clearer but not further thinning. There was modest improvement in reading the eye chart, and corneal staining due to defects was minimized. Intraocular pressure remained normal in both eyes at about 16 mm Hg during this period. The phospholipid deposits further reduced in density and began to give the appearance of lesser areas of concentrations. Nearly functional vision could be achieved by positioning the head back and viewing through the central cornea. The residual clear area of the cornea became more so and less inflamed. Through the end of the second month, improvement to the cornea accelerated. The pupil was now clearly visible and more light was entering the eye. By the third month, the lipid sectors were noticeably reduced and some functional vision was attained.

The patient was examined regularly by an ophthalmologist, and after three and one half months of treatment. The intraocular pressure was normal at 12 mm Hg. The affected eye was considered stable and normalizing. The reduction of the intraocular pressure demonstrated reduction in inflammation. Intraocular pressure has remained in the same range for more than one year.

Example 5: Treatment of Dyslexia and Impaired Executive Brain Function Exacerbated by Traumatic Brain Injury A 52 year-old male patient had been diagnosed in childhood with dyslexia. Symptoms included unstable binocular fixation while reading, the inability without compensating to find the end of one line and beginning of the next, and double overlapping perception of lines of print. He was also unable to read aloud in a fluid manner.

The individual applied a topical gel containing 4% by weight progesterone (4 mg of drug) to the forehead area. The patient reported that within 60 seconds his eyes relaxed into alignment, the effect lasting for hours.

The application was repeated twice over the next few days and the patient tested himself by reading text. The patient reported slightly better and easier reading and line tracking. The treatment benefit lasted for about four hours.

Regular treatment was continued for 10 weeks with the 4% progesterone gel applied to the forehead twice daily. The patient reported that in living with dyslexia for 52 years, he had never experienced as much stress relief in his visual system after the treatment. He was able to track from one end of a line of text to the beginning of the next line without using a ruler for assistance. He can read aloud with less choppiness.

After 8 weeks of treatment, the individual was asked to read aloud a complex paragraph of 8 sentences from his computer screen. His articulation was accurate and fluid with only one word lapse.

Treatment was interrupted after 10 weeks to determine the duration of benefit. Ten days later, the individual reported continued benefit with only slight degradation.

Seven years prior to initiation of progesterone topical treatment, the patient had suffered traumatic brain injury (TBI) in an auto accident. He reported exacerbation of his vision problems as a result of the accident.

After treatment, in addition to improved reading ability discussed above, he experienced improved executive function which is commonly damaged by TBI. He reported a much lower level of stress. After the crash he suffered from post traumatic stress disorder triggered by loud sounds. The patient could not even listen to music because it would induce nausea. Two months after initiation of the progesterone treatment, he regained a good deal of social conformability, improved his ability to organize thoughts, eliminated his disjointed thinking, and gained the ability to write coherently. He also reported the ability to do simple math in his head, having been unable to perform that task for the 7 plus years prior to the treatment.

A 51 year old female who had been diagnosed with severe reading problems in third grade was later recognized as having dyslexia. Her reading problems became exacerbated by an automobile accident in 1980 at 18 years of age, following six months of coma. In general reading was a chore. However she made a concerted effort to learn to read, starting with children's books, and is now able to read regular print. Reading issues were exemplified by the need to place a ruler below each line so that she can follow the line and find the next line, and seeing letters backwards. She is not able to read small print at all. About 4 years ago her vision became worse. She was prescribed glasses that she uses during periods when vision is worse than usual, whether near, intermediate, or far in distance.

A 1% progesterone topical composition was applied to her forehead. About 5 minutes later, she could "feel a clearing in her head". She was able to read without using a ruler or glasses. Her distance vision also improved. When driving that night, she was no longer bothered by the headlight glare from oncoming cars. The effect lasted from the time of application, around 7:30 pm to bedtime at around 11 pm. Reapplication next morning restored vision improvements.

Example 6: Treatment of Symptoms Associated with Alzheimer's Disease

An 84 year old female diagnosed with late stage Alzheimer disease five years ago suffers from episodes of extreme agitation, aggressive behavior, and nocturnal restlessness and disorientation that is difficult for her caregiver to manage. Approximately 2 mg dronabinol was delivered cranially to her forehead.

An improvement in her symptoms were observable within two hours of dronabinol application, including less frequent nocturnal disturbances. Continued daily dosing provided additional significantly noticeable improvement in her symptoms.

Example 7: Treatment of Ocular Discomfort Associated with Dry Eye and Contact Lenses Twenty-seven patients diagnosed with ocular discomfort resulting from dry eye were treated with topical progesterone (0.5%-4% by weight, corresponding to approximately 1-4 mg progesterone per application) applied to the forehead either once or twice per day.

Improvement was seen in all cases. Most patients were able to discontinue previous therapy including eye drops and artificial tears. A summary of clinical results is shown below in Table 2.

TABLE 2

Treatment of dry eye with topical progesterone applied cranially

| Subject | Gender | McMonnies' Score* | Progesterone Formulation Used | Results |
|---|---|---|---|---|
| 1 | F | 27 | 0.5-1% on the forehead, once daily. | Diagnosed with Sjogren's syndrome. Eyes moist and tearing minutes after |

TABLE 2-continued

Treatment of dry eye with topical progesterone applied cranially

| Subject | Gender | McMonnies' Score* | Progesterone Formulation Used | Results |
|---|---|---|---|---|
| | | | | application. Stopped all auxiliary eye drops. After prolonged use, no longer requires. |
| 2 | F | 17 | 1% progesterone BID | Eyes tear minutes after application above the brows. |
| 3 | F | 12 | 1% progesterone BID | Eyes tear minutes after application above the brows. Could stop eye drop use. |
| 4 | F | 9 | 1% progesterone | No noticeable immediate effect but moisture felt after 10 minutes; after weeks of use, no redness or acuity problem after extended computer use as encountered previously. |
| 5 | M | not determined | 1% progesterone | 74 year old male had problem for 3 decades of hypertearing including mucus secretion, photosensitivity, and itching. Could not drive at night due to glare. After 3 months of using product twice a day, all problems were eliminated including itching. Could drive at night again. |
| 6 | F | 14 | 1% progesterone | Previous: Bloodshot eyes and reduced acuity at end of day, discharge in the morning. Started using product before bedtime - prevented discharge in the morning and acuity and redness at end of day. |
| 7 | F | 28 | 1% progesterone BID | Prev. dry eyes with mucus discharge. First day after use, discharge decreased and later stopped. Continued to use product for 2 months until ran out of product - yellow discharge returned when use ceased. |
| 8 | F | 12 | 1% progesterone | Increased tear production, acuity, prevented mucus discharge and redness. |
| 9 | F | 14 | 1% progesterone ON | Suffers from severe dry eye at night that wakes her up without intervention. Had been using petrolatum ointment. Has been applying on forehead over eyebrows. Equally effective. Uses nightly once a day only usually. |
| 10 | F | 18 | 1% progesterone BID | Patient had severe eye problems that affected her vision. Recently diagnosed with Fuch dystrophy, a genetic disorder, and about a week prior had a partial corneal transplant. Post surgery eyes were uncomfortable. Reported relief upon progesterone therapy when used 2-3 times a day. |
| 11 | F | 22 | 1% progesterone BID | Patient had severe dry eyes. Previous regimen: For at least 2 years, Restasis ™ morning and evening. Eye ointment at bedtime. "Oily" eyedrops between 4-5 am each morning. Patient applied 1% progesterone. For first 2 weeks she reported marginal results, but on week 3 she felt that the 1% progesterone adequately replaced all previous treatments. |
| 12 | F | 17 | 1% progesterone | Reported "marked decrease" in "gritty" feeling. |
| 13 | M | 11 | 1% progesterone | Reported product works, prevents "gummy" exudate and eye fatigue. |
| 14 | F | not determined | 1% progesterone | Air stewardess uses twice a day on flights over 6-7 hours for comfort and preventing red eyes. |
| 15 | F | 21 | 1% progesterone | Tear production in seconds. Redness disappeared. |
| 16 | F | 22 | 1% progesterone BID | Extreme hyper-tearing began easing following the first dose, and there was less irritation and dryness next morning. Hyper-tearing completely stopped by the third day. Antihistamine tablet use caused a slight temporary reversal 3 weeks later. |

TABLE 2-continued

Treatment of dry eye with topical progesterone applied cranially

| Subject | Gender | McMonnies' Score* | Progesterone Formulation Used | Results |
|---|---|---|---|---|
| 17 | F | not determined | 1% progesterone TID | Stopped using lubricating drops. Redness, itching and scaly eyelids disappeared. Previously multiple eye surgeries, one to remove calcium deposit. Was also taking glaucoma medications. |
| 18 | F | not determined | 1% progesterone | Began using 2-3 times/day. Eyelids no longer sticky after 2 days of use. Chronic dry mouth gone after a few minutes. TBUT increased from 2 to 8. Long term improvement, only occasional "sticky eyelids". |
| 19 | F | not determined | 0.75% or 1% progesterone BID | Eyes felt "less dry in the morning". Previous ocular grittiness and burning. Past Lasik; concurrent thyroid disease and antihistamine tablets. |
| 20 | F | not determined | 0.75% or 1% progesterone BID | Immediate production of tears, and eyes not so dry in the morning. Previously dryness, grittiness, eye irritation upon waking, artificial tear usual, HRT, thyroid disease. |
| 21 | F | not determined | 0.75% or 1% progesterone BID | More comfort, less red. Previously chronic dryness, burning, irritation with only slight improvement with artificial tears. |
| 22 | F | not determined | 0.75% or 1% progesterone BID | More comfortable, less photosensitive, and less red within two hours. |
| 23 | F | not determined | 0.75% or 1% progesterone BID | Improved eye comfort and eye moisture within half hour. Fewer meibomian cysts along lid margin. |
| 24 | F | not determined | 0.75% or 1% progesterone BID | Increased visual acuity in twenty minutes, less glare, halos and photosensitivity. Previous glare and decreased vision at night, problems driving. Punctal plugs relieved symptoms. |
| 25 | F | not determined | 0.75% or 1% progesterone BID | More comfortable and increased tear production, less red. Previous complaints of "sandy gritty sensation". |
| 26 | F | not determined | 0.75% or 1% progesterone BID | More comfortable and moisture within half hour. |
| 27 | F | not determined | 0.75% or 1% progesterone BID | Improved quality of tears, moisture and comfort. |

*A score of over 20 is indicative of dry eye, while a total score of between 10 and 20 is suggestive of borderline dry eye disease.

Ten individuals reporting ocular discomfort resulting from wearing contact lenses were treated with topical progesterone (0.25%-1% by weight, corresponding to approximately 1-4 mg progesterone per application) applied to the forehead either once or twice per day. All individuals reported elimination of discomfort, irritation, redness, grittiness, and burning. Additionally, individuals were able to wear their contact lenses for a longer period of time as compared to before treatment. The individuals also reported that it was easier to insert and remove their lenses. An improvement in visual acuity was also reported. A summary of clinical results is shown below in Table 3.

TABLE 3

Treatment of contact lense discomfort with topical progesterone applied cranially

| Subject | Gender | McMonnies' Score* | Progesterone Formulation Used | Results |
|---|---|---|---|---|
| 1 | F | 13 | 1% progesterone | Eyes tear minutes after application to either over the eyes or above the brows. Helped with redness. Air conditioning very irritating. Reported that 1% progesterone was effective. Reported product helped with seasonal and feline allergies. |
| 2 | F | 14 | 1% progesterone | Previous: Bloodshot eyes and reduced acuity at end of day, discharge in the morning. Started using product before |

TABLE 3-continued

Treatment of contact lense discomfort with topical progesterone applied cranially

| Subject | Gender | McMonnies' Score* | Progesterone Formulation Used | Results |
|---|---|---|---|---|
| | | | | bedtime - prevented discharge in the morning and acuity and redness at end of day. Contacts used for 1 week felt like new. |
| 3 | F | 24 | 1% progesterone BID | Product eliminated discomfort, irritation and burning due to contact lens wear. |
| 4 | F | not determined | 1% progesterone | Product worked well for eyes. Prolongs contact lens wearing time and comfort. Suffers wet macular degeneration, receiving Lucentis treatment. |
| 5 | F | not determined | 1% progesterone BID | Diagnosed April 2011. Blurred vision, stickiness, irritation with contact lenses >6 hours. Difficult to remove soft lenses at end of day. Refresh 4 times a day provided relief from stickiness only. Moisture in eyes within minutes of treatment initiation. Within days irritation and blurred vision improved. When stopped using, symptoms reappeared. Resumed with 0.25% each night as of beginning of December 2013. Able to wear soft lenses for up to 12 hours/day without irritation, with ease of insertion and removal. |
| 6 | M | not determined | 0.5% progesterone | Redness from contact lens wear immediately resolved after application. |
| 7 | F | not determined | 0.75% or 1% progesterone BID | Moisture and tear production increase within half hour. Improvements in ocular comfort, photosensitivity, redness and grittiness. No longer difficulty in opening eyes in the morning. Can leave contact lenses in all day until bedtime, much longer than before. |
| 8 | F | not determined | 0.75% or 1% progesterone BID | Applied only over the left eye, but both eyes improved within 3-4 minutes. Visual acuity improved. Less discharge in the morning. Lenses "felt like new". |
| 9 | F | not determined | 0.75% or 1% progesterone BID | Had problems tolerating contact lenses. Eyes were moist within 20 minutes of application, and more comfort within 40 minutes. Can wear contacts longer. |
| 10 | F | not determined | 0.75% or 1% progesterone BID | Increased contact lens tolerance and general ocular comfort. |

*A score of over 20 is indicative of dry eye, while a total score of between 10 and 20 is suggestive of borderline dry eye disease.

Example 8: Treatment of Blepharospasm

A 58 year old female had a blink rate averaging 73 times per minute. Upon ophthalmic re-examination following fourteen days of 1% progesterone gel applied topically to the forehead, the blink rate had decreased to 18 times per minute.

Example 9: Treatment of Drug-Induced Eye Irritation

A 68 year old male and a 68 year old female induced eye irritation by applying three drops of 0.05% cyclosporine emulsion onto the forehead. Within five minutes the eyes became irritated and stinging, and the eyelids became heavy. There was no production of moisture. The discomfort intensified with time. Ten minutes later, drug residual was cleaned off from the forehead, and 1% progesterone was applied. Within two minutes, the irritation and stinging began to dissipate.

Example 10: Stimulation of Eyelash and Eyebrow Growth

A 67 year old post-menopausal female had lost all of her eyelashes following chemotherapy and no spontaneous re-growth occurred in the nine years since the treatment ceased. Cranial application of 1% progesterone gel (1 mg) was initiated once daily. After two weeks, her upper and lower lashes began growing and were noticeable. Her lashes fell out after halting progesterone administration. Upon reapplication of at least 1% progesterone daily, eyelash growth resumed. The appearance and disappearance of eyelashes was uniform across her upper and lower eyelids.

A 45 year old female reported eye brow growth after applying 0.75% to 1% progesterone to the forehead for several days.

A 62 year old female reported eye lash and eye brow growth after applying 1% progesterone to the forehead for 3 weeks.

A 67 year old male applied 1% progesterone (1 mg) daily to his forehead and experienced significant growth to the upper and lower eyelashes as a unit. Following one year of intermittent application of progesterone gel once or twice a week, his eyelash shafts were thicker and naturally curled up and down away from the eyes. Since beginning progesterone therapy, there has been minimal lash loss on any of his eyelids. The outer limit for the growth of any particular lash has not been reached and lashes continue to lengthen as a unit. Lashes filled in rows on lid margins where none were apparent and density has noticeably increased. Application of progesterone also resulted in eyebrow growth.

A 74 year old male had lost his eyebrows as a result of Hashimoto's thyroiditis. Application of 1% progesterone gel daily resulted in eyebrow growth within the first two weeks of use.

Example 11: Treatment of Dry Eye in Domestic Animals

A puggle presented with mucus discharge from the eyes. Application of progesterone to the dog's forehead resulted in improved symptoms within 24 hours. After using the daily topical forehead treatment for 4 days, the problem no longer recurred. The owner reported that the dog has this problem spring and fall, which indicates it is allergic seasonal rhinitis. The reported use took place in the fall.

A bulldog diagnosed with Sjogren's syndrome had mucus discharge from the eyes. The dog was being treated with tacrolimus directly in the eye without completely stopping the discharge. Topical application of progesterone was effective within 24 hours, resulting in a cessation of mucus discharge.

Example 12: Treatment of Ocular Discomfort and Promotion of Ocular Health

A 68 year old male and a male between 25 and 45 years old applied a solution containing vitamin A, 1 mg xeaxanthin and 5 mg lutein on the forehead. Ocular comfort as exemplified by lubrication, less lid friction, and less blinking was experienced within fifteen minutes.

Example 13: Treatment of Ocular Discomfort and Redness in Post-Surgical Patients, and Patients on Glaucoma Medication A female >80 years of age had four eye surgeries and was being treated with two glaucoma eye drops (dozolamide-timolol combination and travaprost) together with a lubricating eye gel twice a day. Within one month of application to the forehead of 1% progesterone three times daily, subject was able to stop using the lubricating drops. Redness also disappeared.

A female >70 years of age had multiple surgeries and was diagnosed with Fuch's corneal dystrophy and narrow angle glaucoma. Prior to the latest surgery, when she was almost legally blind, she started applying to her forehead 1% progesterone 2-3 times a day, then reduced the application frequency to once a day. Product helped to ease irritation, lid sticking and redness, some of which was associated with the surgery, glaucoma drops, and steroid drops.

Example 14: Treatment of Drug-Induced Anorexia

A 67 year old male who had taken 20 mg duloxetine HCl (CYMBALTA™) orally for short courses of 7 to 10 days once or twice a year over the course of the last 10 years, experienced drug induced anorexia during the drug therapy. This condition was quite pronounced after the second daily dose, with complete loss of appetite by the third dose. This reaction occurred with every course.

The subject topically applied 2 mg of dronabinol to his forehead daily together with the oral CYMBALTA™. The topical dronabinol prevented the CYMBALTA™ induced loss of appetite over a 2 week course of treatment.

Example 15: Rapid Anti-Anxiety Treatment

A 67 year old male applied 1 mg of midazolam to his forehead on three separate occasions. Each application produced, within 5 minutes, a very rapid response that developed into a state of mild sedation and anti-anxiety. These effects lasted for 4 to 6 hours after application of the drug.

Example 16: Treatment of Pain

A 67 year old female suffered a wrist fracture of the left distal radius and ulnar styloid, with subsequent severe pain. Application of approximately 4 mg progesterone topically to the forehead resulted in a significant decrease in pain within 15 minutes of application.

A 51 year old female was diagnosed 10 years ago with arthritis in her right wrist, with pain, weakness, and limited motion in the hand and wrist. Her ability to cut hair or open bottles, which requires torque, was greatly reduced. The condition has worsened since she was first diagnosed. The individual is being treated with regular steroid injections. Five days after applying 1% progesterone to her forehead, she experienced significantly less wrist pain and increased mobility and strength. She is able to twist open tightly closed containers. Additionally, bone snapping sounds and feelings are no longer present.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

What is claimed is:

1. A method for treating an ophthalmic disease or condition, the method comprising:
    identifying a subject having the disease or condition, and
    administering topically a topical progesterone composition to an area of the face of the subject,
wherein the area of the face is the forehead and the ophthalmic disease or condition is contact lens discomfort.

2. The method of claim 1, wherein a dose of progesterone from 0.01 mg to 20 mg is administered.

* * * * *